US008722090B2

(12) United States Patent  
Klokkers et al.

(10) Patent No.: US 8,722,090 B2  
(45) Date of Patent: May 13, 2014

(54) GRANULATE COMPRISING AN OILY SUBSTANCE, CORRESPONDING PRODUCTION METHOD AND TABLET

(75) Inventors: Karin Klokkers, Vagen (DE); Ina Elfriede Otto, Taufkirchen (DE); Heidemarie Edith Elfriede Meyer, Magdeburg (DE)

(73) Assignee: Hexal AG, Holzkirchen (DE)

( * ) Notice: Subject to any disclaimer, the term of this patent is extended or adjusted under 35 U.S.C. 154(b) by 1225 days.

(21) Appl. No.: 10/541,894

(22) PCT Filed: Dec. 11, 2003

(86) PCT No.: PCT/EP03/14097
§ 371 (c)(1),
(2), (4) Date: Dec. 2, 2005

(87) PCT Pub. No.: WO2004/062644
PCT Pub. Date: Jul. 29, 2004

(65) Prior Publication Data
US 2006/0147529 A1 Jul. 6, 2006

(30) Foreign Application Priority Data
Jan. 9, 2003 (DE) .................................. 103 00 325

(51) Int. Cl.
*A61K 9/26* (2006.01)
*A61K 9/14* (2006.01)
*A61K 9/20* (2006.01)

(52) U.S. Cl.
USPC ............ 424/489; 424/469; 424/464; 424/465

(58) Field of Classification Search
USPC .................................. 424/489, 469, 464, 465
See application file for complete search history.

(56) References Cited

U.S. PATENT DOCUMENTS

| 3,864,362 | A | * | 2/1975 | Feuer et al. ................... 549/403 |
| 4,013,784 | A | | 3/1977 | Speiser |
| 4,128,658 | A | | 12/1978 | Bradshaw et al. |
| 4,132,753 | A | | 1/1979 | Blichare et al. |
| 4,948,589 | A | * | 8/1990 | Iijima et al. ................... 424/438 |
| 5,387,431 | A | * | 2/1995 | Fuisz ............................ 426/658 |
| 5,472,704 | A | | 12/1995 | Santus |
| 5,593,690 | A | * | 1/1997 | Akiyama et al. .............. 424/457 |

FOREIGN PATENT DOCUMENTS

| EP | 0 043 254 A | 1/1982 |
| EP | 0 255 002 A | 2/1988 |
| EP | 0326026 B1 | 6/1992 |
| EP | 0 594 152 A | 4/1994 |
| EP | 0 654 263 A | 5/1995 |
| EP | 0 624 366 B | 5/1996 |
| EP | 0 729 751 A | 9/1996 |
| EP | 0 665 830 B | 3/1997 |
| EP | 0 630 235 B | 6/1997 |
| EP | 1 023 896 A | 8/2000 |
| EP | 0 731 694 B | 2/2002 |
| EP | 0 789 559 B | 10/2002 |
| JP | 09 020686 A | 1/1997 |
| JP | 09 095439 A | 4/1997 |
| WO | WO 92/06679 | 4/1992 |
| WO | WO 93/07859 | 4/1993 |
| WO | WO 96/14058 | 5/1996 |
| WO | WO 98/52684 | 11/1998 |
| WO | WO 99/01111 | 1/1999 |
| WO | WO 99/65471 | 12/1999 |

OTHER PUBLICATIONS

Material Safety Data Sheet (MSDS) for "Vet-A-Mix" (Nov. 19, 1992, pp. 1-2).*

* cited by examiner

*Primary Examiner* — Aradhana Sasan
(74) *Attorney, Agent, or Firm* — Licata & Tyrrell P.C.

(57) ABSTRACT

The invention relates to a process for the preparation of granules comprising an oily substance. It relates also to granules for a pharmaceutical formulation and to a tablet as a product of further processing.

25 Claims, No Drawings

GRANULATE COMPRISING AN OILY SUBSTANCE, CORRESPONDING PRODUCTION METHOD AND TABLET

This is a 371 filing of International Patent Application No. PCT/EP2003/014097 filed Dec. 11, 2003 and published on Jul. 29, 2004 under publication number WO 2004/062644 A and claims priority benefits from German Patent Application No. 103 00 325.8 filed Jan. 9, 2003.

The invention relates to retard formulations for corrosive and/or hydrophilic active ingredients. In accordance with the invention, the preparation of such retard formulations is carried out using a granulator by spraying a mixture of active ingredient(s) and retarding agent(s) with an oily substance.

One possible method of obtaining retard formulations usually comprises the preparation of tablets or capsules that comprise the pharmaceutical active ingredient dispersed in a matrix. The matrix forms a continuous phase around the active ingredient and in that way allows its gradual release. An advantage of a retard formulation is the uniform and prolonged effective level of active ingredient during release. The time interval between the individual ingestions of tablets is longer for retarded pharmaceutical forms than it is for rapid-release formulations. Improved patient compliance can thus be achieved.

Methods that are known for the preparation of retard formulations having a lipophilic matrix are especially, inter alia, melt granulation and melt extrusion.

EP 0 630 235 B1 discloses the melt pelletisation procedure. In a plowshare mixer, the active ingredient is processed with water-insoluble, wax-like binders (m.p. >40° C.) to form pellets. According to EP 0 654 263 A1, only a small yield of pellets in the desired size range is achieved in that way.

An improved process for preparing sustained-release particles by melt granulation is described in EP 0 654 263 A1. Active ingredient particles are mixed in a high-speed mixer with a meltable carrier (e.g. oils, waxes, m.p. 35-150° C.) and optionally with a release-controlling component (salts, lactose, HPMC), the carrier material being softened by a supply of energy. The cooled agglomerates so obtained are brought to a diameter of <2 mm. The mesh size of the sieves must not be too small, otherwise they become blocked by the agglomerates melting under pressure. The sieved particles are softened again in the high-speed mixer, with the result that the fine particles are taken up by the larger particles. A small percentage of the carrier can be added again. In that way a good yield of particles of a particular size and having a uniform rate of release is obtained, especially for substances that are very readily water-soluble. The rate of release decreases, of course, after compression of the particles to form tablets.

In accordance with EP 0 789 559 B2, the process of EP 0 654 263 A1 can be improved in terms of yield, active-ingredient loading and uniformity of the particle size when the agglomerates of active ingredient and meltable carrier are extruded.

EP 0 731 694 B1, EP 1 023 896 A2, EP 624 366 B1 and EP 729 751 A1 describe matrix formulations for tramadol comprising hydrophilic/hydrophobic polymers, substituted/unsubstituted $C_8$-$C_{50}$ hydrocarbons (fatty acids, vegetable oils, waxes) or polyalkylene glycols as retarding agents. The sustained-release matrices can be prepared, for example, by wet-granulation of the active ingredient with cellulose derivatives, mixing of the granules with fatty alcohol and subsequent compression and shaping of the granules. A coating technique is also possible. The active ingredient can also be pelletised, for example in a plowshare mixer, using a binder having a melting point above 40° C. (for example hydrogenated vegetable oils).

U.S. Pat. No. 4,013,784 relates to retard formulations having a fat matrix of triglycerides with $C_{12}$-$C_{18}$ fatty acids. Using a high-speed mixer, the active ingredient is dispersed with calcium salts in one (or more) molten triglyceride(s). The granules can be prepared from the dispersion by means of a high-pressure atomiser, a vibrating nozzle or by allowing to cool into plates and subsequently cutting into pieces.

U.S. Pat. No. 4,132,753 describes the preparation of sustained-release granules by means of infra-red irradiation of a mixture of powdered active ingredient and finely particulate, wax-like material in a "rotating tumbling cylinder". In that procedure, the active ingredient is heated above the melting point of the wax-like material and sinks into the wax-like material, which has not yet melted.

WO 92/06679 discloses an improved melt-granulation process in which the active ingredient in cohesive form (particle size <20 μm) and, for example, a lipophilic binder are used. Pellets having low porosity can be obtained in that way.

WO 93/07859 and WO 96/14058 describe the preparation of sustained-release matrix formulations with the aid of melt-extrusion technology.

EP 0 043 254 A1 relates to the use of a low-melting lipid and a high-melting lipid in the preparation of a matrix-retard formulation with the aid of extrusion or granulation technology. The objective is for there to be little thermal loading of the active ingredient.

WO 99/01111 discloses a sustained-release tramadol formulation having a stable release profile which is achieved by "curing" the solid matrix formulation comprising wax-like substances for a specific period of time at a specific temperature. The preparation is preferably carried out by means of extrusion and pelletisation.

WO 98/52684 describes an improved melt-extrusion process which uses an integrated special cooling zone in the screw extruder.

A tramadol-retard formulation comprising a fatty alcohol as matrix-forming agent is described in EP 0 914 823 A1. In the fatty alcohol, a matrix-forming agent was found that makes it possible for the active ingredient to be released over a period of 24 hours. Here, the active ingredient is mixed with microcrystalline cellulose in a fluidised bed granulator and sprayed with a solution of the fatty alcohol in isopropanol. After sieving, readily free-flowing granules are obtained which are compressed to form tablets.

WO 99/65471 describes a process for the preparation of retard tablets in which a liquid oil-in-water emulsion is sprayed onto a powder mixture comprising active ingredient or onto granules. The fat-coated granules so obtained are compressed to form tablets. Only the tablets, but not the granules, exhibit delayed release of active ingredient.

In EP 0 665 830 B1, the problem of the corrosiveness of tilidine hydrochloride semihydrate is bypassed by using tilidine dihydrogen orthophosphate. Unlike the hydrochloride salt, the phosphate salt is not at all hygroscopic and therefore does not react with and corrode metal materials.

Advantages of melt extrusion are a) a high active ingredient loading, even for water-soluble active ingredients, b) a high density and c) a low porosity of the pellet surface or particle surface and, associated with that, a good retardation. Extrusion is accordingly a method that is often selected for the preparation of retard formulations.

A disadvantage of the extrusion method is that, when the molten masses cool, because of the different physical properties of the components, on the one hand dissociation may occur but, on the other hand, when oligomeric or polymeric substances are used, molecular weight degradation may also occur. The latter may result in the retarding polymer having a limited effect. The product homogeneity is also frequently unsatisfactory.

Melt extrusion is a continuous process with high energy consumption and is therefore time- and cost-intensive.

Both in the case of melt-embedding in a heatable mixer and in the case of the extrusion method, the large number of process steps and the problems of dust at the interfaces of the different process steps are a disadvantage. The embedded materials or extrudates so obtained are generally too coarse for direct further processing. They need to be sieved under complicated conditions, that is, production is time- and cost-intensive. Using such methods additionally involves undesired thermal loading of the active ingredient-containing mixtures.

The fluidised-bed granulation of active ingredients with fats or waxes in accordance with the hitherto known processes yields granule particles that are not very compact and are very porous and that do not exhibit sufficient retardation of the release of active ingredient.

There are particular problems in the processing of corrosive active ingredients. An example of a corrosive active ingredient is tilidine hydrochloride, which is strongly hygroscopic and reacts with metal surfaces (e.g. tablet dies). In the preparation of tablets or granules using such active ingredients, particular requirements therefore have to be met in respect of air-conditioning of the operating rooms and protection against corrosion of the apparatus and tools employed.

The problem underlying the invention is to provide a simple and effective process for the preparation of retard formulations with the aid of granulators in which the formulations are to have a defined sustained-release profile for the active ingredient(s). The objective is for it to be possible in general for the preparation process to be used for various active ingredients and different release profiles. A further intention is for the process to be suitable for corrosive and/or hydrophilic active ingredients.

According to one embodiment, the problem underlying the present invention is solved by a process for the preparation of granules for a pharmaceutical formulation wherein
 (i) a mixture comprising or consisting of
  one or more active ingredients and
  one or more retarding agents
  is wetted with an oily substance and
 (ii) the mixture is granulated.

According to a further embodiment, the problem underlying the invention is solved by a process for the preparation of granules for a pharmaceutical formulation wherein
 (i) one or more active ingredients are mixed with one or more retarding agents,
 (ii) the mixture obtained is wetted with an oily substance and
 (iii) the mixture obtained is granulated.

There can be used in the process according to the invention a mixture (i) according to the first embodiment or a mixture (ii) according to the second embodiment comprising one or more excipients, especially one or more fillers, flow-regulating agents, wetting agents and/or disintegrants.

Furthermore, wetting with the oily substance in the process according to the invention can be carried out by spraying.

In addition, wetting with the oily substance in the process according to the invention can be carried out at room temperature.

Also, in the process according to the invention, at least one corrosive and/or hydrophilic active ingredient may be provided for the mixture (i) according to the first embodiment or for the mixture (ii) according to the second embodiment. An example of prior art corrosive active ingredients is supplied by EP 0 665 830.

Furthermore, in the process according to the invention an active ingredient content of from 0.1 to 98% by weight and especially from 0.5 to 70% by weight (based on the total weight of the granules) may be provided.

Also, in the process according to the invention there may be provided, as retarding agent for the mixture (i) according to the first embodiment or for the mixture (ii) according to the second embodiment, a lipophilic retarding agent or a fat matrix-forming agent, especially in combination with a hydrogel matrix-forming agent and/or structural matrix-forming agent.

Also, in the process according to the invention there may be provided, as retarding agent, a combination of fat matrix-forming agent and hydrogel matrix-forming agent.

Also, in the process according to the invention there may be provided, as retarding agent, a combination of fat matrix-forming agent and structural matrix-forming agent with water-soluble excipient.

Furthermore, in the process according to the invention there may be used, as the oily substance, a natural oil, a synthetic oil, a solution of wax in oil, or a low-viscosity wax.

Also, in the process according to the invention a content of oily substance of from 0.2 to 20% by weight and especially from 1 to 7.5% by weight (based on the total weight of the granules) may be provided.

Also, in the process according to the invention the resulting granules may in addition be provided with an outer phase of one or more retarding agents.

In the process according to the invention, in addition granulation may be carried out using a fluidised bed granulator or a plowshare mixer.

In the process according to the invention, granulation may furthermore be carried out with the aid of a granule binder, especially in the form of a solution (granulating solution) of the granule binder in a solvent.

Finally, in the process according to the invention the granules obtained can be further processed to form tablets.

According to a further embodiment, the invention relates to a process for the preparation of tablets in which granules that have been obtained in accordance with a process according to the invention for preparing granules for a pharmaceutical formulation are processed to form tablets.

In the further processing of granules according to the invention to form tablets or in the preparation according to the invention of tablets, excipients may be used, especially fillers, lubricants, flow-regulating agents and/or disintegrants.

Finally, a tablet obtained in accordance with the invention may be provided with a coating.

According to a further embodiment, the invention relates to granules that have been obtained in accordance with a process according to the invention.

According to a further embodiment, the invention relates to granules for a pharmaceutical formulation in which the granules consist of or comprise a mixture of
 one or more active ingredients and
 one or more retarding agents, wherein
 the mixture has been wetted with an oily substance.

The granules according to the invention may contain or comprise at least one corrosive and/or hydrophilic active ingredient.

Finally, the invention relates to a tablet that has been obtained in accordance with a process according to the invention.

Surprisingly, it has now been found that adequate retardation and good processability of an active ingredient can also be achieved by means of granulating processes when a mixture of active ingredient(s) and lipophilic retarding agent(s) (=fat matrix) are sprayed with an oily substance prior to or during granulation. The oily substance wets or film-coats the surface of the active ingredient particles and renders them hydrophobic. The non-tacky granules so obtained can readily be further processed, for example sieved and tabletted. As a result of the active ingredient being embedded in a fat matrix in combination with an oily substance, direct contact of the active ingredient with the tool surfaces is avoided, that is, it is also possible for corrosive active ingredients to be processed into granules. In addition, the formation of impurities, which is catalysed by contact of the active ingredient with metal ions of the tool surfaces, can be substantially reduced by that manner of embedding active ingredient. The combination of fat matrix and oily substance leads to an especially good embedding of the active ingredient(s). This results in a good retardation of the release of active ingredient.

Granulators that can be used are fluidised bed apparatuses or plowshare mixers. Preferably, granulation is carried out in a fluidised bed apparatus.

In the process according to the invention for the preparation of retard formulations, first of all the active ingredient(s) is/are mixed in a fluidised bed granulator with at least one lipophilic retarding agent (=fat matrix-forming agent) and optionally one or more excipients (for example fillers, flow-regulating agents, wetting agents and/or disintegrants). The resulting mixture is sprayed at room temperature with an oily substance. A binder-containing granulating solution is then sprayed onto the particles. In the spraying operation, the temperature of the particles consisting of active ingredient(s), retarding agent(s), optionally excipients and oily substance can be from 30 to 40° C. The granules so obtained can optionally be provided with an outer phase of one or more retarding agents. After drying and sieving, free-flowing granules having a uniform particle-size distribution are obtained.

The following may be mentioned as preferred examples of corrosive active ingredients: tilidine hydrochloride, ranitidine hydrochloride, clindamycin hydrochloride, doxepin hydrochloride, citalopram hydrobromide, amitriptyline, cetirizine and piroxicam. The corrosive active ingredients can be used in the form of pharmaceutically acceptable salts, hydrates, solvates as well as in the form of derivatives. The corrosive active ingredients can also be used in combination with further non-corrosive active ingredients. A combination of tilidine hydrochloride and naloxone hydrochloride is preferred.

The active ingredient contents can vary within wide limits in accordance with the active ingredient employed and the desired rate of release. For example the active ingredient combination may be in the range from 0.1 to 98% by weight, preferably from 0.5 to 70% by weight, based on the total weight of the granules provided for a pharmaceutical formulation.

The retarding agents include fat matrix-forming agents, hydrogel matrix-forming agents and structural matrix-forming agents.

Suitable lipophilic retarding agents (=fat matrix-forming agents) are, for example
- fatty alcohols, such as stearyl alcohol;
- mono-, di- and tri-glycerides, such as glycerol monostearate, PRECIROL (glycerol palmitostearate) or COMPRITOL (glycerol monobehenate with 0.2-0.3% magnesium stearate);
- hydrogenated vegetable oils, such as hydrogenated castor oil (CUTINA HR);
- waxes, such as beeswax, carnauba wax or microcrystalline wax.

As preferred lipophilic retarding agents, glycerol monobehenate and/or hydrogenated castor oil are/is used. The fat matrix-forming agents are present in concentrations of from 5 to 60% by weight, especially from 10 to 50% by weight, based on the total weight of the pharmaceutical form.

In combination with one or more fat matrix-forming agents there may also be used hydrogel matrix-forming agents, such as, for example, hydroxypropyl methyl cellulose, hydroxypropyl cellulose, ethyl hydroxyethyl cellulose, hydroxyethyl cellulose, methyl cellulose, alginates, CARBOMER (polyacrylic acids), sodium carboxymethylcellulose, tragacanth, rubber or gelatine. Those polymers are able to hydrate and form a gel-like layer that is capable of releasing the active ingredient slowly by diffusion and erosion.

In a further matrix form that releases in controlled manner, the active ingredient(s) is/are embedded together with water-soluble excipients in a structure formed from water-insoluble indigestible excipients. By dissolving out the soluble constituents, pores result through which the active ingredient can diffuse to the outside. As structural matrix-forming agents, polymers such as, for example, ethyl cellulose, cellulose acetate or polymethyl methacrylates, can be used.

Preferably, a combination of fat matrix and hydrogel matrix is used.

Suitable oily substances are neutral oil, sesame oil, peanut oil, olive oil, almond oil, castor oil, soybean oil, coconut oil, cottonseed oil, corn oil, rape oil, sunflower oil, wheat kernel oil and liquid paraffin. Wax solutions in organic oil, or low-viscosity wax, can also be used. Neutral oil is especially preferred. Neutral oil (MIGLYOL) is understood to mean a mixture of short- and medium-chained triglycerides, mainly with the fatty acids caprylic acid (C8) and capric acid (C10). The MIGLYOLS also include esters with propylene glycol. MIGLYOL 812 is preferred. The oily substances are present in concentrations of from 0.2 to 20% by weight, especially from 1 to 7.5% by weight, based on the total weight of the granules.

The following excipients can be used in the granule preparation: flow-regulating agents, such as, for example, AEROSIL, talc; granule binders, such as, for example, gelatine, starch paste, methyl cellulose, carboxymethyl cellulose, hydroxypropyl methyl cellulose, hydroxypropyl cellulose, pectin-slime, polyvinylpyrrolidone, polyvinyl acetate and/or polyvinyl alcohol; dry binders, such as, for example, microcrystalline cellulose, starch, modified starch, lactose and/or saccharose; solvents for a granulating solution, such as, for example, water, ethanol, isopropanol, acetone or mixtures thereof; disintegrants, such as, for example, sodium carboxymethyl starch, crospovidone; wetting agents, such as, for example, sodium lauryl sulphate or sodium docusate.

The granules according to the invention can be further processed to form tablets.

The following excipients can be used for the tablet preparation:
- fillers, such as cellulose and/or cellulose derivatives (for example microcrystalline cellulose), sugars (for example lactose, glucose, saccharose), sugar alcohols (for example mannitol, sorbitol), starch (for example potato starch, wheat starch, maize starch and/or rice starch),
- lubricants, such as magnesium stearate, calcium stearate, stearic acid, hydrogenated vegetable oils and/or talc,
- flow-regulating agents disintegrants.

The tablets may have a coating.

The invention is explained in detail by the following Examples without, however, the scope of the invention being limited thereby.

EXAMPLE 1

The following substances are used to prepare tilidine hydrochloride tablets.

| Constituents | Percentage (%) | Weight (mg/tablet) |
|---|---|---|
| Tilidine hydrochloride semihydrate | 25.7 | 102.87 |
| Naloxone hydrochloride | 2.3 | 8.80 |
| Hydroxypropyl methyl cellulose | 10.5 | 40.00 |
| AEROSIL | 0.5 | 2.00 |
| Hydrogenated castor oil | 17.9 | 68.50 |
| COMPRITOL | 17.0 | 64.89 |
| KOLLIDON | 1.96 | 7.50 |
| Neutral oil | 5.0 | 19.11 |
| Purified water | | 150.0 |
| TABLETTOSE | 16.6 | 66.38 |
| Magnesium stearate | 0.52 | 2.0 |
| Total | 100 | 382.1 |

Tilidine hydrochloride semihydrate, naloxone hydrochloride, hydroxypropyl methyl cellulose, AEROSIL, hydrogenated castor oil and COMPRITOL are weighed out, sieved and then mixed in a fluidised bed granulator. The resulting mixture is sprayed in the fluidised bed granulator with neutral oil and then with a granulating solution of KOLLIDON in water. The granules so obtained are dried in the fluidised bed granulator. After sieving through a 1 mm sieve, readily free-flowing granules are obtained. The granules are mixed in a free-fall mixer with TABLETTOSE and magnesium stearate and compressed to form tablets each weighing 382 mg.

EXAMPLE 2

The following substances are used to prepare tablets comprising tilidine mesylate.

| Constituents | Percentage (%) | Weight (mg/tablet) |
|---|---|---|
| Tilidine mesylate | 29.8 | 119.25 |
| Naloxone hydrochloride | 2.2 | 8.80 |
| MICROCELLAC | 17 | 67.95 |
| Hydroxypropyl methyl cellulose | 10 | 40.00 |
| AEROSIL | 0.5 | 2.00 |
| Hydrogenated castor oil | 17.1 | 68.50 |
| COMPRITOL | 20 | 80.00 |
| KOLLIDON | 1.9 | 7.50 |
| Castor oil | 1 | 4.00 |
| Purified water | | 150.0 |
| Magnesium stearate | 0.5 | 2.00 |
| Total | 100 | 400.0 |

The preparation of the tablets is carried out analogously to Example 1.
Release Profile
Apparatus for determining tilidine release:
Cell: basket
Medium: 0.2M phosphate buffer pH=6.8
Temperature: 37° C.
Stirring speed: 150 revs/min

| Time/min. | Released tilidine in % |
|---|---|
| 30 | 40 |
| 60 | 62 |
| 120 | 77 |
| 180 | 82 |
| 240 | 85 |
| 360 | 88 |
| 480 | 90 |
| 600 | 91 |
| 720 | 92 |

EXAMPLE 3

The following substances are used to prepare tablets comprising tilidine mesylate.

| Constituents | Percentage (%) | Weight (mg/tablet) |
|---|---|---|
| Tilidine mesylate | 31.2 | 119.25 |
| Naloxone hydrochloride | 2.3 | 8.8 |
| Hydroxypropyl methyl cellulose | 10.5 | 40.00 |
| AEROSIL | 0.5 | 2.00 |
| Hydrogenated castor oil | 17.9 | 68.50 |
| COMPRITOL | 17.0 | 64.89 |
| KOLLIDON | 1.96 | 7.50 |
| Neutral oil | 5.0 | 19.11 |
| Purified water | | 150.0 |
| TABLETTOSE | 13.1 | 50.0 |
| Magnesium stearate | 0.52 | 2.0 |
| Total | 100 | 382.1 |

The preparation of the tablets is carried out analogously to Example 1.
Release Profile
Apparatus for determining tilidine release:
Cell: basket
Medium: 0.2M phosphate buffer pH=6.8
Temperature: 37° C.
Stirring speed: 150 revs/min

| Time/min. | Released tilidine in % |
|---|---|
| 30 | 29 |
| 60 | 46 |
| 120 | 62 |
| 180 | 69 |
| 240 | 74 |
| 360 | 81 |
| 480 | 85 |
| 600 | 88 |
| 720 | 90 |

The invention claimed is:
1. A method for preparing granules for a pharmaceutical formulation comprising wetting a mixture of one or more corrosive active ingredients and one or more lipophilic retard- ing agents by spraying the mixture with an oily substance selected from the group consisting of neutral oil comprising caprylic and capric acid triglycerides, sesame oil, peanut oil, olive oil, almond oil, soybean oil, coconut oil, cottonseed oil, corn oil, rape oil, sunflower oil, wheat kernel oil, liquid paraffin, wax solutions in organic oil, and low viscosity wax; and granulating the wetted mixture so that granules for a pharmaceutical formulation are prepared.

2. The method of claim 1, wherein the mixture further comprises one or more excipients, fillers, flow-regulating agents, wetting agents or disintegrants, or a mixture thereof.

3. The method of claim 1, wherein the step of wetting the mixture is carried out at room temperature.

4. The method of claim 1, wherein at least one of the active ingredients is hydrophilic.

5. The method of claim 1, wherein the active ingredient content is from 0.1% to 98% by weight of the total weight of the granules.

6. The method of claim 1, wherein the active ingredient content is from 0.5% to 70% by weight of the total weight of the granules.

7. The method of claim 1, wherein the lipophilic retarding agent is combined with a hydrogel matrix-forming agent, structural matrix-forming agent, or combination thereof.

8. The method of claim 1, wherein the lipophilic retarding agent is combined with a structural matrix-forming agent and water-soluble excipient.

9. The method of claim 1, wherein the content of oily substance is from 0.2% to 20% by weight of the total weight of the granules.

10. The method of claim 1, wherein the content of oily substance is from 1.0% to 7.5% by weight of the total weight of the granules.

11. The method of claim 1, wherein the granules further comprise an outer phase of one or more retarding agents.

12. The method of claim 1, wherein the step of granulating the wetted mixture is carried out using a fluidized bed granulator or a plowshare mixer.

13. The method of claim 1, wherein the step of granulating the wetted mixture is carried out in the presence of a granule binder.

14. The method of claim 1, further comprising compressing the granules into tablets.

15. A method for preparing tablets comprising wetting a mixture of one or more corrosive active ingredients and one or more retarding agents by spraying the mixture with an oily substance selected from the group consisting of neutral oil comprising caprylic and capric acid triglycerides, sesame oil, peanut oil, olive oil, almond oil, soybean oil, coconut oil, cottonseed oil, corn oil, rape oil, sunflower oil, wheat kernel oil, liquid paraffin, wax solutions in organic oil, and low viscosity wax; granulating the wetted mixture so that granules are formed; and compressing the granules so that tablets are prepared.

16. The method of claim 15, further comprising mixing the granules with at least one excipient prior to the step of compressing the granules.

17. The method of claim 16, wherein the excipient is a filler, lubricant, flow-regulating agent, disintegrant, or a mixture thereof.

18. The method of claim 15, wherein the tablet further comprises a coating.

19. Granules prepared according to the method of claim 1.

20. Granules for a pharmaceutical formulation comprising a mixture of one or more corrosive active ingredients and one or more lipophilic retarding agents, wherein the mixture has been wetted by spraying the mixture with an oily substance selected from the group consisting of neutral oil comprising caprylic and capric acid triglycerides, sesame oil, peanut oil, olive oil, almond oil, soybean oil, coconut oil, cottonseed oil, corn oil, rape oil, sunflower oil, wheat kernel oil, liquid paraffin, wax solutions in organic oil, and low viscosity wax.

21. Granules according to claim 20, wherein at least one of the active ingredients is hydrophilic.

22. A tablet prepared according to the method of claim 15.

23. The method of claim 1, wherein the one or more lipophilic retarding agents are selected from the group consisting of a fatty alcohol, a hydrogenated vegetable oil, and a wax.

24. The method of claim 15, wherein the one or more lipophilic retarding agents are selected from the group consisting of a fatty alcohol, a hydrogenated vegetable oil, and a wax.

25. The granules of claim 20, wherein the one or more lipophilic retarding agents are selected from the group consisting of a fatty alcohol, a hydrogenated vegetable oil, and a wax.

* * * * *